US00PP13352P2

(12) United States Plant Patent
Sherman

(10) Patent No.: US PP13,352 P2
(45) Date of Patent: Dec. 10, 2002

(54) PEACH TREE NAMED 'UFO'

(76) Inventor: Wayne B. Sherman, University of Florida, P.O. Box 110690, Gainesville, FL (US) 32611-0690

( * ) Notice: Subject to any disclaimer, the term of this patent is extended or adjusted under 35 U.S.C. 154(b) by 1 day.

(21) Appl. No.: 09/618,270

(22) Filed: Jul. 18, 2000

(51) Int. Cl.[7] ..... A01H 5/00
(52) U.S. Cl. ..... Plt./197
(58) Field of Search ..... Plt./197

*Primary Examiner*—Bruce R. Campell
*Assistant Examiner*—Michelle Kizilkaya

(57) ABSTRACT

A new and distinct variety of peach tree, which has a low winter chilling requirement of approximately 250 chill units (cu). The tree is large size, highly vigorous with a semi-upright growth habit, and has showy pink flowers. Glands are small and reniform in shape and isolated to the basal portions of leaves. This tree, which has been denominated 'UFO', is a regular bearer of heavy crops which are large for the moderately early ripening season, with yellow and very firm non-melting fresh, semi-freestone fruit of peento shape. Fruit are uniform, attractive, substantially symmetrical shape, and have an attractive 50 to 70% striped red skin color. The fruit ripens 10 to 15 days after 'UFGold' in mid- to late May at Gainesville.

1 Drawing Sheet

BACKGROUND OF THE NEW VARIETY

The present invention relates to a new and distinct variety of peach (*Prunus persica* (L.) Bastch) tree named 'UFO', and more particularly to a peach tree adapted to a mild winter climate. The tree produces peento (donut, flat or saucer shape) fruit with good eating quality, semi-freestone, and yellow, non-melting flesh, maturing in mid- to late May at Gainesville. Asexual propagation was performed at Gainesville, Fla., where the selection was made, and top worked trees were fruited the past two years. Contrast is made to 'UFGold' (U.S. Plant Pat. No. 10,315) peach, a standard variety, for reliable description and contrast. This new peento peach variety is a promising candidate for a unique fruit on the fresh market. It retains fruit firmness at the full flavor, tree ripe stage for 10 days on the tree.

ORIGIN OF THE VARIETY

This peach tree (genotype) originated in the fruit breeding program at the University of Florida, located at Gainesville, as a self-pollination of Fla. 95-10pc (non-patented), a non-melting flesh peach from the program. 'UFO' was observed with a crop in 1997, and was selected from about 30 siblings in 1998 when it bore a heavy crop and was determined to have unique tree and fruit characteristics making it worthy for commercial fresh fruit production. It was designated as Fla. 98-7pc and was asexually propagated at Gainesville as a uniform variety by topworking 3-year-old trees and by budding to young seedlings of 'Flordaguard' (non-patented) rootstock. There are no effects of this rootstock on this scion variety that are known to the inventor.

SUMMARY OF THE VARIETY

The new and distinct variety of peento peach bears yellow, non-melting flesh fruit, and has a moderate-chilling dormancy requirement estimated to be 250 chill units based on time of bloom in relation to standard varieties. 'UFO' blooms about 5 days after 'UFGold' peach at Gainesville, bearing 50 to 70% red skin and yellow flesh fruit. When grown in subtropical climates to take advantage of its early bloom (low-chilling), 'UFO' is the first described, non-melting flesh, peento peach to ripen in the USA.

The present invention resulting in 'UFO' peach tree is characterized by non-melting flesh, peento shape, and attractive fruit of excellent flavor and eating quality on a tree adapted to mild winters. The trees are vigorous, productive, and regular bearing. Trees attain in two years, a height of three meters and a spread of two meters at Gainesville. The first fruit ripen in mid-to late May at Gainesville, about 95 days from full bloom, which is about 10 to 15 days after 'UFGold'. The fruit are uniformly large (60 to 80 g) for a peento peach. Ripe fruit have 50 to 70% red (solid and stripes) skin with small flecks of red pigment in the flesh, but no red in the flesh surrounding the pit. The flower anthers are light red to yellow, a common characteristic of many standard peach and nectarine varieties.

BRIEF DESCRIPTION OF THE DRAWING

The accompanying drawing is a color photograph which shows a typical specimen of the fruit, leaf, and stem of the new variety as nearly true as it is reasonably possible to make in a color illustration of this type. The photograph shows an attractive shape and exterior coloration of three specimens of fruit above a ruler in a stem end view, a blossom end view, and a fruit cut lengthwise at the suture.

DETAILED BOTANICAL DESCRIPTION

The tree, flowers, and fruit may vary in slight detail due to variations in soil type, cultural practices, and climatic conditions. The present botanical description is that of the variety grown under the ecological conditions prevailing at Gainesville, Fla. Colors (except those in common terms) are described from "The Pantone Book of Color" published by H. N. Abrams, Inc., N.Y. 1990.

Tree:

*Size*.—Trees are large when pruned to form an open vase.

*Vigor*.—Highly vigorous, and must be summer and winter pruned to keep tree height restricted and to keep center of vase open.

*Density*.—Medium dense in branching habit. Pruning is required to get high sunlight into the tree interior for formation of strong fruiting limbs and high fruit color and sweetness.

*Form*.—Semi-upright and easily pruned to form a vase shape.

*Bearer*.—Regular and generally requires fruit thinning to obtain the desirable larger fruit size.

*Productivity*.—Fruit set is usually two or more times the amount desired for normal tree crop load.

Trunk:

*Size*.—Medium trunk diameter attaining 7 cm diameter at a height of 30 cm at the end of 3 years growth at Gainesville.

*Texture*.—Medium smooth, but changes to medium rough as tree ages.

*Bark color*.—Gray older bark, Chinchilla (Pantone 17-1109).

*Lenticels*.—Numerous, small (2–4 mm), with the center being Mineral Yellow (Pantone 15-1046).

Branches:

*Size*.—Strong growth of scaffold branches.

*Texture*.—Relatively smooth, medium amount of lenticels attaining size found on trunk and old scaffolds.

*Color*.—New wood is light green, Leek Green (Pantone 15-0628); Old wood is light brown, Chinchilla (Pantone 17-1109).

Leaves:

*Size*.—Medium; 15 to 19 cm length, including the petiole; 3 to 4 cm width. Measurements on vigorous upright shoots of summer growth.

*Thickness*.—Regular and average for commercial peach varieties.

*Form*.—Lanceolate.

*Apex*.—Acuminate.

*Margin*.—Serrulate, slightly undulate.

*Base*.—Cuneate.

*Surface*.—Upper, glabrous; Lower, medium large veins.

*Color*.—Lower surface is green, Cedar (Pantone 16-0526); Upper surface is darker dull green, Peridot (Pantone 17-0336).

*Glands*.—Four to six large reniform glands mostly on lower leaf blade and on petiole.

*Petiole*.—About 1 cm (1.0 to 1.4 cm) length and 1.5 to 2 mm diameter, being slightly larger diameter at the base. Petiole is dull green, Dusky Dull Green (Pantone 18-0840) on mature leaves of summer growth.

*Stipules*.—There are usually 2 stipules attached at the base of each leaf petiole, averaging 1 cm length, usually abscising by the time the leaf becomes full size. They are light green, Seacrest (Pantone 13-0111).

Flower buds:

*Abundance*.—Moderately high, most buds produce flowers that set fruit in absence of spring frosts.

*Size*.—Medium, average 3.5 mm length.

*Form*.—Plump, conic.

*Surface*.—Pubescent scales.

*Color*.—Grayish brown, Stucco (Pantone 16-1412), in late winter.

Flowers:

*Blossom period*.—5 days after UFGold peach; average February 8 to 12 at Gainesville, but occurring over a 7 to 10 day period. Time and length of bloom is dependant on ambient temperature.

*Aroma*.—Slight to none.

*Type*.—Non-showy, location and seasonally variable within the range of commercial non-showy varieties. Average flower diameter is 24 mm. Average petal length is 9 mm and width is 6 mm. There are 5 sepals and 5 petals. Sepals are pubescent and petals are glabrous.

*Color*.—Petals and flower are pink, Orchid Pink (Pantone 13-2010) at first opening, darkening to deep pink, Geranium Pink (Pantone 15-1922), toward the flower center before petal abscission, and within the range of standard varieties.

*Calyx cup*.—Medium as compared to commerical varieties, averaging 5.5 to 6 mm diameter at point of petal attachment.

*Anthers*.—Light red to yellow, regular size.

*Pollen*.—Abundant, bright yellow (common to many varieties) and self fertile.

Fruit:

*Maturity when described*.—Tree-ripe, May 22, 2000, at Gainesville.

*Date of first picking*.—May 20, 2000, at Gainesville (normal).

*Date of last picking*.—May 30, 2000, at Gainesville.

*Size*.—Uniform, medium large (large size for early maturity at 60 to 80 g).

*Average equatorial diameter at the suture*.—2½ inches (63 mm).

*Average polar length (height)*.—1 inch (2.5 mm).

*Stem*.—Averages 5 mm length and 4 mm diameter.

*Form: Longitudinal section form*.—Flat oval.

*Transverse section through diameter*.—Rounded.

*Suture*.—Shallow, narrow cleft that is conspicuous from stem to apex.

*Ventral surface*.—Rounded sides to a cleft or slightly indented.

*Base*.—Retuse in amount similar to apex.

*Apex*.—Depressed nearly to pit.

*Cavity*.—Flaring circular.

*Cavity depth*.—¼ to ⅜ inch (6 to 9 mm).

*Cavity breadth*.—9/32 inch (6 mm).

Skin:

*Thickness*.—Medium in comparison to commercial peach varieties.

*Texture*.—Fine in comparison to commercial peach varieties.

*Tenacity*.—Tanacious to flesh even when over-ripe.

*Color*.—Dark red, Barn Red (Pantone 18-1531) to bright red, Mandarin Orange (Pantone 16-1459) between stripes cover 50 to 70% of skin. Ground color is deep yellow, Sunset Gold (Pantone 13-0940).

*Tendency to crack*.—None observed on ripe fruit.

Flesh:

*Ripens*.—Evenly within each fruit and throughout the tree.

*Texture*.—Firm, juicy, non-melting when fully ripe.

*Fibers*.—Very fine, tender, and small.

*Aroma*.—Moderate and in the middle range of commercial peach varieties.

*Eating quality*.—Good, sweet, and sub acid.
*Juice*.—Abundant.
*Color*.—Radiant Yellow (Pantone 15-1058) with small red flecks in flesh, but no red surrounding the pit.
*Browning by oxidation*.—Slight on soft ripe fruit.
*Amygdalin*.—Undetected.

Stone:
*Type*.—Semi-freestone, pulling free from the flesh at softening ripe.
*Size*.—Medium small; average width — 20 mm wide perpendicular to the suture and 22 mm wide at the suture.
*Average polar length*.—13 mm.
*Color*.—Light brown, Gold Earth (Pantone 15-1234), when freshly exposed.
*Form*.—Peento shape similar to fruit.
*Base*.—Straight.
*Apex*.—Near flat.
*Sides*.—Near equal.
*Surface*.—Single furrow both at the suture and on the ventral edge.
*Ridges*.—Flattening toward the base.
*Pit wall*.—3/16 to 1/4 inch thick (5 to 6 mm).
*Tendency to split*.—None observed.

Use: Fresh; dessert.
Resistance to disease: High resistance to bacterial spot incited by *Xanthomonas campestris* pv. *pruni* (Sm.) Dye. Resistance to other fruit and tree diseases are not noted to be any different than other varieties grown in Florida.
Keeping quality: Excellent after 2 weeks at 45° F.
Shipping quality: Degree of firmness at harvest and firmness retained in refrigeration at 45° F. for 2 weeks indicates fruit should be highly acceptable for shipping.

The potential for commercial production of fresh fruit is high because of its peento shape, attractive red skin, early ripening, good flavor, and exceptional firmness related to its non-melting flesh.

We claim:

1. A new and distinct peento peach tree variety as illustrated and described, characterized by a low-chilling requirement, and bearing early-ripening fruit with firm, yellow, non-melting flesh of high eating quality and an attractive, high percentage red over color and with fruit ripening in mid- to late May or 10 to 15 days after 'UFGold' at Gainesville.

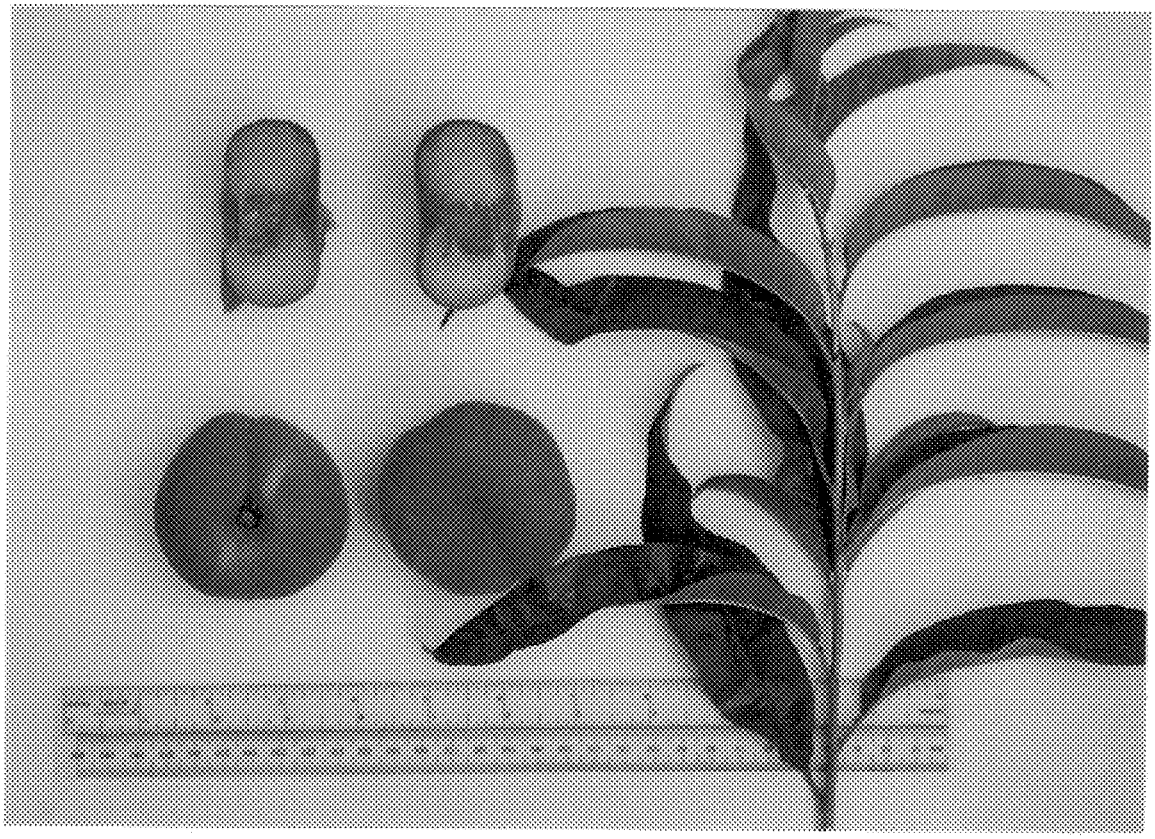

* * * * *